United States Patent
Yoon et al.

(10) Patent No.: US 11,351,210 B2
(45) Date of Patent: Jun. 7, 2022

(54) LACTOCOCCUS GARVIEAE BACTERIOPHAGE LAC-GAP-3 AND USE THEREOF IN INHIBITING PROLIFERATION OF LACTOCOCCUS GARVIEAE BACTERIA

(71) Applicant: INTRON BIOTECHNOLOGY, INC., Gyeonggi-do (KR)

(72) Inventors: Seong Jun Yoon, Seoul (KR); Soo Youn Jun, Seoul (KR); An Sung Kwon, Gyeonggi-do (KR); Soon Hye Hwang, Gyeonggi-do (KR); Hyun Min Song, Seoul (KR); Sang Hyeon Kang, Seoul (KR)

(73) Assignee: INTRON BIOTECHNOLOGY, INC., Gyeonggi-Do (KR)

( * ) Notice: Subject to any disclaimer, the term of this patent is extended or adjusted under 35 U.S.C. 154(b) by 612 days.

(21) Appl. No.: 16/330,562

(22) PCT Filed: Aug. 21, 2017

(86) PCT No.: PCT/KR2017/009077
§ 371 (c)(1),
(2) Date: Mar. 5, 2019

(87) PCT Pub. No.: WO2018/048114
PCT Pub. Date: Mar. 15, 2018

(65) Prior Publication Data
US 2021/0322494 A1 Oct. 21, 2021

(30) Foreign Application Priority Data

Sep. 6, 2016 (KR) .................. 10-2016-0114167

(51) Int. Cl.
| | |
|---|---|
| *A61K 35/76* | (2015.01) |
| *A61K 9/00* | (2006.01) |
| *A23K 20/195* | (2016.01) |
| *A23K 10/16* | (2016.01) |
| *A61P 31/04* | (2006.01) |
| *C12N 7/00* | (2006.01) |
| *A23K 50/80* | (2016.01) |

(52) U.S. Cl.
CPC .............. *A61K 35/76* (2013.01); *A23K 10/16* (2016.05); *A23K 20/195* (2016.05); *A23K 50/80* (2016.05); *A61K 9/0017* (2013.01); *A61K 9/0056* (2013.01); *A61P 31/04* (2018.01); *C12N 7/00* (2013.01); *C12N 2795/10311* (2013.01); *C12N 2795/10331* (2013.01); *C12N 2795/10371* (2013.01)

(58) Field of Classification Search
None
See application file for complete search history.

(56) References Cited

U.S. PATENT DOCUMENTS

2018/0000125 A1    1/2018   Yoon et al.

FOREIGN PATENT DOCUMENTS

KR    10-2012-0118570 A    10/2012
KR    10-2016-0088650 A    7/2016

OTHER PUBLICATIONS

Hoai, T.D. et al., Properties and Genomic Analysis of *Lactococcus garvieae* Lysogenic Bacteriophage PLgT-1, a New Member of *Siphoviridae*, with Homology to *Lactococcus lactis* Phages. Virus Res. 2016; 222:13-23.

Nakai, T. et al., Protective Effects of Bacteriophage on Experimental *Lactococcus garvieae* Infection in Yellowtail. Dis Aquat Organ. 1999; 37(1):33-41.

Park, K.-H. et al., A Virulent Bacteriophage of *Lactococcus garvieae* (formerly *Enterococcus seriolieida*) Isolated from Yellowtail *Seriola quinqueradiata*. Dis Aquat Organ. 1997; 29:145-9.

International Search Report and Written Opinion dated Feb. 8, 2018 by the International Searching Authority for Patent Application No. PCT/KR2017/009077, which was filed on Aug. 21, 2017 and published as WO 2018/048114 on Mar. 15, 2018 (Inventor—Yoon et al.; Applicant—Intron Biotechnology, Inc.) (Original—8 pages; Translation—5 pages).

*Primary Examiner* — Nicole Kinsey White
(74) *Attorney, Agent, or Firm* — Ballard Spahr LLP (57) ABSTRACT

The present invention relates to Siphoviridae bacteriophage Lac-GAP-3 (Accession Number KCTC 12816BP) having the ability to specifically kill *Lactococcus garvieae* bacteria and a genome represented by SEQ ID NO: 1 and isolated from nature, and a method for prevention and treatment of *Lactococcus garvieae* bacterial infection by using a composition containing the same bacteriophage as an effective ingredient.

2 Claims, 1 Drawing Sheet
Specification includes a Sequence Listing.

SEQUENCE LISTING

```
<160> NUMBER OF SEQ ID NOS: 1

<210> SEQ ID NO 1
<211> LENGTH: 24375
<212> TYPE: DNA
<213> ORGANISM: Unknown
<220> FEATURE:
<223> OTHER INFORMATION: Siphoviridae bacteriophage Lac-GAP-3 (Accession
      number: KCTC 12816BP) isolated from nature
<220> FEATURE:
<221> NAME/KEY: gene
<222> LOCATION: (1)..(24375)
<223> OTHER INFORMATION: Siphoviridae bacteriophage Lac-GAP-3

<400> SEQUENCE: 1
cgatagggtc agcgtctttt gttatttccg aaccgtctga aaagtgatac gttatttcag      60
ttatcttctt tccttctggt ataacccagt tttcattctt ccgatctata ctcgctcaac     120
tcctcatcta attctctaag ctcatttct aaactttcaa tctcgtccca agcttcatca      180
agtctgcatt caaggttttc gttttcctct cggagttctt ccaactctgc ttcaagctct     240
tcaatttctg cattcttgtc tttgatcatt tcgttaagtt cttcgatctt ttcacgacct     300
tcctcaactg ttctaactac catttaattt tcctccaatt tataaacttt gtattttcct     360
tcttgtggtc gttttgaccg tttacgcttg ctatcctttg ctaactgatg aaattgaagc     420
attgagatac caaggaagtt agcaagctct ttagatgttc ctaagtcaat gaatatttca     480
tctccatcgt gagccttgta aagaatgtac tctttcattt attcgctcct ttcttcataa     540
catcatggat aacacatacc cccatgaata acacaaatgc tacaattccc gctaaattca     600
ttttccttcc tcctcgaaat gtttagttac agcaacacta gcattataca agccagtgat     660
aaactttcta aatacaaaga atgcaataac tgcaagtaca ataaatgtca acatttttta     720
cctccaattt gtttatttaa tgttaggtca agtgtgataa gttccgctta tctcgtgtgc     780
tttatttatc ttacatacat agtataacaa taaaaaaagc ccctgtcaat gacaagagct     840
ttaaacttaa attacaaggt tgttacagta caaggaattg aataaatggg gtaataacct     900
actttctatc tagtttatca atcatttatt aaagtaactt tgccttgttt tcctaagtcg     960
tctaaaaact ttgttgcttc tccctcttct aaatcttccc ccttctctac tttgacagtc    1020
ggatctataa tcgtaaattt atcgtcaaca tatccgacac atatcggctt atcataatta    1080
aaattacggg cttccacttc aataatagaa tatttgttcc ccgtcttttt gcttatctta    1140
ggtgacagcg taaagcaaac ttcatgccat gcaccaatag cggaactgcc taaagcgtgc    1200
gtgctccgtg tcctaaataa tggttcttct aatgaacgat caaaacaatc tttccgagcg    1260
tgagcaacta ataaaaaggt gacatcacca aacattaatt ttagtttggt tatcctcatt    1320
agaagctcat tcattttgtg catgtcattt aaagcgtctg gtgagcttat catatctttt    1380
agacagtcta gtatcaccac tttgatatta agttgtttta ttgcgctgta aagcttattc    1440
atgtgtctct tatcatctag cttgaatata ccacctgtga ggaaatacaa gccctctaat    1500
```

```
gagccgtcat agccatttaa tcgttggtgc aatgtaaatt ctgtatcctc gttatcaatg    1560
ataaggacat tcgcttttgt tgtttcatgc tctccaaatg gttgccctgt tgcgatggca    1620
tgtgccataa acaaggtaga tgaactttta aagctttttt gaggtgcaac gaccagaccg    1680
ccaactcctt taggtaaaat atctttgata taccatgaat tagcgtcttt aaaatcgtct    1740
ttctctttta gctcctttgc ggttatcagc cttttaaacg ggtcattatc gaccgctgta    1800
aagcctatgc tgtctaaatt aattgcgtgg gtgttttctg ttattgaatt caatctttaa    1860
ttctagcgct cttttccaag ctctcaaagt ggttttatta tttaccgcct tatgtagcct    1920
tagagctttc ctttctaagt ttgttgtaag acctatccaa cgtgtgatga tgtcttgcct    1980
tattatatca tcttcaagaa ctctttcacc gattgtataa acccagccgt acaactcaac    2040
aaacaacttt acagcatgtg cctcgtaact ttcgttttta tttttcatct aaagcccaac    2100
ctcctatgta agcaatggca ctaataaaca gatataagac accctgtgca atgctaccat    2160
caataaagca agttagggat aacactgcca tgaataccc gatgacacaa agtaccaaca    2220
tcaaattatc attatctatc atgctttctc ctcataaaaa tctttttttaa atttatattc    2280 tcggcaattg ttacagtaat atctttctaa aaccagatca tcacaaaaaa ctctttcatc    2340 acacttttg caatacttta taccggttgt ttttttacca ccgaatataa ctcttcctaa    2400
caagtcacct ataccactag ccactataac aagcgctaca agcccacaaa taacatttac    2460
tacatctaac attaatactc ctccaaccat tctacaaaag tcaacaataa gagcaataca    2520
cccattgtaa accatactaa aaataaatta tgtgcattga taattgataa caagaacgca    2580
ccaaaagcac aaagtaaata aacgtatttc atttctatac ctctcttttt attttataat    2640
tgttcggaca agtttttttt aatatgggaa ctttataacc tcatgtcttt gtattattaa    2700
tatatcacac tttaaaacca atgtcaagta aaaaaagcat aaaaaaagag aaattctttt    2760
agagaactcc tcttgtaatc aaatagcttt atttatattt tgcccttttg cctattcggg    2820
ttttacccct tataccccctt atcgtgtatt ataaaccgta ctttaatagc tccacctaat    2880
aggatatttc gccttagatt tcctagcctt aaagccttat gcttataatc gtcacggagt    2940
gtttctcttc tcgacactca tggaagcctt agcggttggc aaacaggtct agggacattc    3000 tccttttag ctttatgtcg cacgcttttt ctatgcctct tgtttataac gtgcacgacc    3060 tcaaagtta ccactaggaa ggctttcgat actcactacc ttattcagta tagttttttc    3120
taatgtcgga tataacaagc ctatcagtta taaccctatt taattacact attattataa    3180
catacgtttt taacttttcc ccatttttttg tgcactttat gtacatttgt ctaaaatcca    3240
ataacaaagc catttactaa catctttga acactttgta cacatttgtc taattttgtg    3300
caccaattct attatatcaa aatataaaaa taaagtcaag cttttttgcac cgtgtataat    3360 agttattgtg attgagggag gtaatcactt atgaaaagta aatatatctg tcctaccaaa    3420
gaggattacg aagaagcgaa atctttctta tggcgtgagg acattattaa aaaaatagaa    3480
tacgatatag acggtaacta tgccgtgata catacggagg aattgccgat ttgaaaaaga    3540
ttttaagtat tgattttagt acaggatcta gcagtggtga gggtacgggg tacgctttcc    3600
gagataatga gggtaaactt atttatggct ctattcaacc ttataaacga gggtctacca    3660
tgcacagtcg tacagaggtt atagtagaag ctatacaaga tattatttta aactatgaac    3720
tacaaagcta tgcatctgt atagaaaagc ctatccttgc aggtaacaaa ggtagaagca    3780
ttgagttagc gcaatggaac ggttatttcc tgggcatggc tcacagtcta acagagggcg    3840
gtgtttataa tatccctaat ggtaaatggt gttcttatca ccttattaaa ggtaaacgac    3900
```

```
aagagcgcaa agatgaaagc tgtcgtctag tatctgaatt aatcggatgt gaaacagatg   3960
acgacaatat ggcagacgca gtcaatcaat tgctttattg cgaagcagtg gactatacac   4020
aattttatta aggaggtgaa taagtgatac catttgttca agtggaaaca cctaatgtaa   4080
atgtgccagc tcaaagtggt tggtgtttga aatatgtaga cgacgggtg aatgctccta    4140
atcgtcaacc gagtgcgcaa gcttcttggg agtatgcaaa gaaaacaggt gtcgcacatg   4200
caaaccaaga accgccaaac aatgtttggg tacccgttta ttattcaatt gatagcggtg   4260
tttatgcagg attgggcat gtagcttggt attattcaga cggcaagaca actaagattt     4320
acgatagtga gtttggttca ggtcgtcgta atcgtccata tggtggaggc gctgagctaa   4380
ttcagttcat gggttataaa atgagctact taggttgggc agaggctgtg gacggtaaag   4440
ttatggtcaa gaaagatcct aaagaggaag ctattaattt attcaaggag gtaaaaatgt  4500
tttttgtaga aacagcagac actaaaaata tctatgtagt taatcaaggt ggctattaca   4560
gtcgagtgcc taaccccgct gtacttacga acatgcgcaa ggcttacggt tgggcaacgt   4620
gtaagatgac acaagcagaa cttgacagca tgtttaagaa atttaagtga ggtggttaga   4680
tgacttataa cccgcttaga ccacaagcgg aagatgtaag ttttcaagt ttcacggtat     4740
ccaatccgac aactgattta atactacaaa agtgtttagg tcttgtatct tattttgacg   4800
gtatcaactg gaaagacgca ggtgcgatta atgacttatt tactttgct ctaacgggtc     4860
aagaagtata taaatcagt ttaggggct ttccttatta cggacttaga gttaatggta      4920
atcaatttaa tatctatgtc cgagaaccta ataagcgtat ggttacggtt cgtgctgata   4980
gctttgaatt gatgtataac cctttctatg gtgcaaaccc tagacgcttt agctcattgt   5040
ttggcatggc ttctaatggt gttggtcgta ggttggatag tcaaggtcaa attaaagtct   5100
attggcatac taaagtggca agcgggctta agaggtttg ggataggata aaagaacggc     5160
tagaccgtat gacagagctt gcgagagctt ataagggcat gacggtagtt agcgacactg   5220
acaaaattac acaaatgcaa cccgactatt caggaagtgt taaaaatgac ggtgagttag   5280
ctattgatat tgctctagct gaatacggta tgcctaggga actcctatac ggcaactcta   5340
acgaggtgtc tttgattacg tttattatcc aaaagataca acctctaatc aaacagcacg   5400
ctccggacgc tgaatttaat cgtgaaaact ttgtagctta tatctctaca actggaaagg   5460
acggaggttt aaacagtgcc aaaagtaaag gcaattcggg ggatagcaaa ccccttggga   5520
acactggaca gccataaaac ggtagtcgaa agtgtaaaga atgcaggtga aggggtagac   5580
atttgcaacc gacaccgcga gaaaatcgga gacgggttta tccacgtcga ggacggcaat   5640
cttattctta ctggttacgt tcgtgaggac gcatacgagg gtagtttaga agaggcgggc   5700
ttgtctattg gttggaatgc attagacatg aaagcccgtg aggctgacgg aatcgcattc   5760
tataaagatg ttgttattaa agaagtatcg ttgaccccgc taccaagtaa caaaggtgct   5820
aaagtcacaa tggtacgaga agaagaaaaa ggagaaatta aaaaaatggg tgaaaatcaa   5880
aacggacttg atgtagtagt gtcgcaatta gcaacagcca tggctgaaaa gatgaacctt   5940
gaaacaaagg tgcgagaatt ggaagacgca caagcagaac ttaaaaagga acgtgaagct   6000
catatccaaa cggacacagc acaagataat agcgaaatgt tttaccgtga gttgggcgag   6060
caaatgaaac aaacgccaga gaaagcattc ttgcgtgagt tcacaaatgc gtctgatcta   6120
gctgtatcta accaacttgg ttcaatcgtt acacaatggg cttctaagtc ctcactcttt   6180
gcggggcta caaaagcacg tttccagggt ttgactttgg cagatgacgg cgacgacggt     6240
gtatttaaac gtgacctctt cacagcaggt ggagataaaa aagagtcgct tacacctact   6300
```

```
aaacgctccc tccgtcctca aatggcttac gcttatatgg aaatggataa agggactgta    6360
tctggtgtag atgatacggg cgaactttct aaatacgtta tgtatgtatt gcctcaacgt    6420
gtcctcaatc aaattgagta caacatgatt tacggtaagg ccgacgggtc taatggtatt    6480
tacggtcttg cgggtggcca caccgataat tggacgcctc aaattgagta tgatttgact    6540
aagactgacc tttttgaagt attgacagac gctatcgcag aagttactta ctctcaaaac    6600
gttgtcgttg taatgcaccc acgtgattac gctaaattgc gtaaagcaaa aggttctgat    6660
ggtcactcac gctttaacga gcttgcgact aaagaacaaa ttgctaactc atttggtgcg    6720
gtagaattgc aaacacgcgc ttggatgaaa gaaggcgata ttgcaatgta tatcaaagat    6780
gagtttgtgc ttattggtga cttggatatg aacaactatg cagactttga cttgcgttac    6840
aacgttgatc aatggttggc agaaatgctt gtcggtggtt ctatccgtgg tcgtggtcgt    6900
tctgtattct tgaaagcaaa agcagcagca gataaaggat aagaaagggg tagttaatgg    6960 cttatttttaa cgtaacagac cgttatagcc agactatcac aagtgtgtta gaggggcaaa    7020
cttacgagca gttccctcta ttgtcacgct tgcgagtgat tgaaagtgat gtattgcaaa    7080
cgttcgacat tgtggacggt cttgcaggca actttgaaac gaaagtgtta ggtgacggga    7140
aagcctatac ggaagaagtt gttttttcata taacggtga tattcacag ggtgctatca    7200 atgtagcagt gaaccacatt gtacgcaact tgtataagaa acttgaaaaa gacatggtag    7260
acagtgcttt ggctcatagc tctaagcctt atgtgcaagg ttttagtgac attatcttga    7320
ctgataataa cgactatgtg cagttagctg taccaaaata tcaagtggat tatttcacag    7380
gaaaaacaat cgcaattaat ccagatactg gtgtactgtt cggggagatt actcctcata    7440
ttgtggtaag catggatatg caacacaata agttaaagt ctatggtact atgcgttgct    7500
taggtgcttg gtattcagac aatgttacaa aagagttagg agggactaat taatggctta    7560
tgaagctttg aatgaattga cacacggctt aggttatggc gtcgtattct tgaaaggttc    7620
gggttcaacg gttgagggtg tgcctattgc gggcttgcgt gctattgata cagaaaacaa    7680
tcaagaaaat gttaactttt atgcgggatt taatgccccg tatcgtacta ttgcaggcgc    7740
gttaaaacgt gaaatcactg taaaatctta tgacctacca cctaagtttg cttctcacgc    7800
tttgggattt gcgtcagcag gtggtacgtt catggtcgac gatacaacat cgtacaagcc    7860
ttatgggttt gcttatgctg aacgtttccg tgatgatgaa aagactggtt acaaagttac    7920
tttctatcct agcgcacaag cgaccacacc aagcgacagc gcacaagcag acgaagaaag    7980
cccaacgggt aaagaatacg agcacaaagc gactattaca agtggtaact tgttgttaa    8040 tggtaaagcc cgtttgttgg ttaacttcat ggtgtcagat gatgatttaa agcgggtac    8100 aagcaaagag gctaaagcat ttgaaaaaat gttttctact ttgcaaccta ttgcgccaga    8160
agatattggc gaaacaacag tagggggttg atttgtgtta gcgagggagg gcttggaaat    8220
aatagtttcc ctcgttttat tttattactc gacaaaggag gtaagagatg ttaaaggaag    8280
attttgtatt ttcttatgaa gcattggcaa agttagaaga tttcggtatc aactttatga    8340
acataccaag cgacgacttt ttacaaatag cccgcttcta ttgggcttgc tgtgatgaca    8400
aatacacgaa agaagaaata ttgcatgctg taacacatgg taaaatgcct ataacaatgg    8460
gtgagattat ggagcgttat atgtcggagg ataaacctaa gaaaaaggc gaggtagtaa    8520 ttatcccaga tgcacagcag gagcttaata caagccaaat aagcgcagtt tgtgcctctc    8580
ttggtataac atatccaacc tatgctaaac gaccgttaaa atggacatta gggctaatta    8640
agaagatgtt gccaaaagag aaaactaaaa caacggcgga ggaacttaat caagcggagc    8700
```

```
atgtcgaggt gaaactatgg caaagaccac aataaacccc gaaaaagtag taggtaagat    8760
aacaggtaag ttagcgcacg atattgcaca ggtacataac aataacctag ctgacatcaa    8820
aaagacctac acgagcgatt taggaggcga ttttagccgt tatcctgtga agtttgatac    8880
agataagctt aaaccgcaaa cacgtgctta tggctcaatt aaaggcggtc tgattggtta    8940
tatcaacggt ttcgatagta aggacgaaag ttggcgcatg cttaatgtat tggcacatga    9000
tagacagtta caccaacgat acagcagaca tctagtaaaa gcgaacttct attacagttc    9060
aaacgcacaa aagattagac gacaaatacg ggggctttta taatggcaaa ggaaaaatat    9120
gtaatccaga ccgagcttga aacaaaacgg ctttgtcgg acgcaaaaac actacaaaaa    9180
gaaataaatg agatcggacg ggttgccaag tccgctagta agaacgctaa aataactggt    9240
aaagtcgaga tgaaagacaa ggctattaag gacacagaaa aagcccttgc aatggctaaa    9300
aagaatgtcg accaacttac acaatcttta gcaaaagtta aaatgaatgg cggtacagag    9360
aaacaagtat caagcctaga aagtcaatta cgtaaggcgc aaataagtgc gaacaactta    9420
gaaagtgaat tgcaccaact taaaggggta gatgttgcac caagggaat ggataaaatc    9480
aaggagctgt tctcgtttgg tagctcacag agtgggatag ggctcaagct tttagatatt    9540
ggctctaagt tctctatgat tgggtcattt ggtttacaag cctttaacgt gattggcggt    9600
gctgttggtc gtgcaaaaga cgcagtggtc gggtttggtc agcgtttaat ggatacgtat    9660
gacactcaac tgagcgctca aaaatccctt tctgtgacat tggcggacgg tgcaaaaggt    9720
tatgaagcat ttaataaaag gatcgagagc ggctctcttt tgcttcaatc acaacgtaat    9780
gacctagcag agttggcaag tttcatttct ggttatgtaa aagtgacagg tgaagaagcc    9840
tttgagattg taaatgctat taataccgtg ggtgatagct taggtctttc aatggataca    9900
caaaaacaat ttacttacgg tcttttcacag gctttgggtg caggtgtatt acatgcgcaa    9960
gactttaacc aaattatgca agctcactt ggtgcacagt tccgtgattt acttattgaa    10020
gcggctaacg agttgcaagg cgttgctatg agtgctaaag agttaccaga tgcaatgaaa    10080
gagggtaagg ttagcgctaa ccaactagcc gatacattcg gttcagattg ggctaagaaa    10140
atggcgaaaa cacaagaggc aaataaaggc tttaaggttt ctgtaggtga cattaaacga    10200
caactcaaag agggtaaact aacagtcgaa gacttcgcaa atgtgttggg ttctgatttc    10260
tctactaagt tgcttaatgc aatgaacgca caagagcaag gaactatcac aatggataac    10320
tttaagcaag ctatggagga cggtgtattt aataccgaag ttatgaacct agcgcttgaa    10380
aagttcaaga agcaagcaga agatacggct aacagtggtc aaatcacatt tacacaaatg    10440
aaagagatga ttacaaaagg gtttgatact tccgctctta gtggttttca atcagagtta    10500
acgagtgcag gctttagcat gggtgagttg ggcgacagtg ctacaaatct ttctatgctt    10560
gtcggtgaaa aaatgggtca aatagcgggt tacgttgtga ataacgtgct taaaatgatt    10620
gacgctaacg gagacggtga agtgtcaaac gaggaactcg ggaaagcgtt cgataaggta    10680
gcaggtaaag taacggacgc ttattacgaa gttcgtaatt tcctaaagca aatacgttgg    10740
tcagatgttt cgggctttgt cggtgacatg ggcgaaatgg ttcgggcttt aatgcagtta    10800
atagattgga ttgctgacgc tatacgttgg atcgaccgtt tgaatgacgc tctaccaaaa    10860
gttaagagta cagaggaaag tcttaaaagt tttggtattg gttcgggtgg tatctttggt    10920
attggtaacc tattcagact acaaagcgat ttaacaggta ttgacaatca attagacggg    10980
gttacagaaa agctatacgg ctcaatggct aagcctttag gaatgaattt acaattgttc    11040
ggtaactatg agaaagctac cgctaacttt atgtcaaatg ttccacaagg tatgaacggg    11100
```

```
tcaacaggct tcacaaatgc cactgtaaca acagataaca gcagtcacaa ggctgtaatt    11160
aatgtttacg gtaacgatag taagaagatt gctgatgaca tttacaagaa attagaaagg    11220
aacggtataa agttaccacg tagataatgc caatatataa aaaaggtgat atatacggct    11280
ctaaaatgtg gaaagattac agcgataagt gtaaaaatga ggtcggacac tgtgaaagat    11340
gttataagac ttatgacctt atagcgcacc acgttgagcc gatacaatgg aagaacggag    11400
tagttgaggc ggaaagcaga gaggcgctta tatatcagcc tatcgaggtt gtgtgccatg    11460
cttgccacca gtcagcagaa agaagcgggg ataatgtaaa ttacgcaaga ttgatagcag    11520
aggggaggat ataaaggtga gtaggttaac agagtggata ggggatagtt ctaaagaatg    11580
gggggcggaa attgtagctc taaaagaaaa agccctaaaa attgagcatg aaatagatta    11640
cgaaaaagcg gaaagcattt ttaacttctt agaaacttac atgactttgc caaataatga    11700
acggtttaaa atcataccgt accacaaggc agtgttaacc ttaactttt gtatcccta    11760 tgatgttagc gaagttgtag ttatcgttgg tcggtcaaat gctaagtcca ttcttgatgt    11820
catgatagca ttagttgaga ttttttttatt acctatgccc aatgctgtta tcgctcttat    11880
ggctaccaaa aaagaccaag cacaacaaat tctaatgaag cactttagag ccatggcgaa    11940
cacagacggc acgattataa acctgtttca aaaccaaatt aagattaatc aagataaaat    12000
caaggtcaag gataattctt tcttggatag taaaggcacg gagataaccg tatatgcttc    12060
aaatgaggat agcttggacg gtggacggga acagcttgta attatagacg agtttggagc    12120
attcaaaaag aacccactta tcactatcag acagggg ctt agaaaaaata aggggctact    12180
ctttatatca acgactaaca acgttattag gggtggtgct tatgatgacg agcttaaaag    12240
ttggaaagaa tgggcaagaa atgaagacta tacacgttgg gttttctatt atgccttaga    12300
tgattatgag gaagtacaca aacccgaaat gtatacaaag gcaaacccg ctatcggtct    12360 tacagtgaca ttagaggaca tacagagcga ctttattgga gctttaggta atcccgttaa    12420
aatggctaaa gttattacta aacgttttaa tttgagcatg cacgatacta caagtatctt    12480
ctcaaaacaa atggttgaca atgctttatg cgatacgcta gatcctagtg gaaaattagt    12540
cgtcattggt tcagacttct ctattcgtgg tgatgtgtgg ggttctgtta tggtgtggag    12600
agaagacggg cattactatg tcaaggctat ccctatcatg ccagagagtt cagaagatag    12660
atacagacac ttaggtgaaa ctatcacgca cagcacagac agtaacaaga gtgatgaagc    12720
ttgggagatg ttcatgacac ggggagtaaa agacgctatc ccaattgctt tatgttatga    12780
cagcaaacac gctacaaatt tcttgcgtag gtttgaagaa agttatgaca tagaatatta    12840
cgaagaagtt aaacaaaact cttttccactt gtctaacacg ctcgaaaaca tgcaattact    12900
tatgcaagaa ggacggttac attttgatag ccaactctta ggggttcact taatgaatgc    12960
ggaaacggtc attaatgact ttggtttaat gcgtatcaag aagaaaggat atgcagataa    13020
gatcgaccta gcggacgctt taagtgacgc tatgtggtgg tttattgaaa aagaagaata    13080
tgcggaggat ttctttagtt aatgattaca gaaaatgata aaaagaaaat gctagaagct    13140
ttggaaacat tggcttacgg tggggatgaa gtaaagagg ttgtgcaata tcaacgaggg    13200
gctaacggtc gagatgttgt aaaagggaag aatgtcacta caacccacaa gctaccagat    13260
aagcaagcat tatttaagct tatggagatt aagggtgtat atatcgagcc taaggttgaa    13320
aaagctaaga atgcactaga agaagaaaaa caagagcgta acttagaaga tttcgtaaaa    13380
aacttgaaac tgaattagga gggtattaaa tgggtacata ttacacagca tattgttata    13440
acccagaaaa tgggtacgat ttcggcaaag agcaacaagt accgccaaac ttaatggaaa    13500
```

```
ctagcgattg ggaaaattat ggcaatgtca accctcctaa acccaccaca aaacaaaata    13560
aacaatttga gcaaatagac agcaatatgc gggcggatat tactaaggag agtgtttatc    13620
cttggtttaa agaaactgga cgaaccaaag cgcaggtctt gcgttgtaag agtacggtag    13680
aggtagatag tgacagttat tacgtaggaa tgcacatgtg tacctttaat tgggtatata    13740
ccccagctca attaaaagca ggcactgtta taactatgag cgtttatgtg tataataacg    13800
acgattacgc atacccttt aacacacgga caaatgaaag caatgatcct cttgtttgga    13860
atggcgcaag tgaaaacaca gcgggtacaa gtattcgcat tgagcctaaa acatggaaac    13920
gcctagaatg gcagtacacg cttaaatatg accatatagg ttcttttagc gaagtaggtg    13980
acttaggtat gcgtgtatat caagaaaaac tctcacaagg tatcaaagcc gattttctta    14040
taggcatgcc taaggtcgag gtaggaataa aagcaacgcc ttacagaatg accgatgggg    14100
aagagaaaag tacagcctat tggactacaa aagacccgta ttatcgccct tatgttggca    14160
gagctacaac agatagcgac aattgggaag attatacagg ttgggaaaaa gtatccgagg    14220
aaattttaga caataaatac gctgatattg gttggactaa agcagaggcg catatagtta    14280
tcttgccaga aagtgcgaat gtagctagtg accgcattaa tatgtgggtt ggtattgata    14340
gcgatacgtt tgatgtcggt acaggtcgca cagttcaatt ttcacaactt aacatggatt    14400
ataactttgt agggcaggtt gtagaatgtg caacagacaa taacggtgct tataactata    14460
atgatagtac atgggtgaat atgggggata ttatgtattc atcacaaaat gggctattaa    14520
tcgaccctgt tttaggtgaa atgggtaact taggtcaaga tgggtcacaa tttacaacag    14580
gtactctgac acgtgtggac gaagttgcac gggatttaat tgttaaccaa ggggcaagtt    14640
atacgggagc ttttgctaac gtagattaca cgaagaagc acaaagtttt agggtaaaaa    14700
cacaagacct caaagtggct agtgcgacat atccagacgc aagcggggga gcttcaagtt    14760
atattgaaaa catatggaat tatggtatga ccacaaaacc atataaagtt aatcgcttca    14820
caactaagtc tacttggact aaaggtatgt ctaattttat ttacaacaac ggcataacct    14880
attttagtcg cattcacaat gacttggcgg actggtttag aggtggtaat atcggtgaca    14940
ttaaaccatt acctcaacgt atcatgatga ttaatatgac tactaaaaaa tggtggtggt    15000
ttgattatga taaaaagcaa gggctttggg tgcgtagtgc agagaaatca cggtcaacaa    15060
ctgcccctac attaattagc acagcatacg ctaacggttt accaaaggac gggaagttaa    15120
aaggttcaat tgtcttcact gacactaatt acacagatta tgcttctaag aacttgccta    15180
gcacattggg gcttgacatt cttttcccag acgaaagaaa agagtttgtt tattatgctc    15240
cgttttggca cgatggtaat tatacaagtg acatgaattg gtgggggct acctcggcag    15300 ttagaactaa tttcgcttac aataatcaaa aatacggtaa gtttggagta tctgcaatta    15360
atttaatgaa cggcacatgc acaatgcgaa gagtgtggaa tagttagaaa ggttacaaaa    15420
tgggtaatac atattacgga aatatgaaag atgttaggtt aataagtgag ataacgggt    15480 ttgatatcga ttttataat ccccttgact ttttaaacta tggtgtatca gagctagaag    15540
caactgtatc acgtgactta tttaagtaca tgtttacgcc taatcatacg ctaataggtc    15600
aatacacgaa cttggagcta ggttgcagta ttctatatat ggttgaccct aagcaatgca    15660
cacgtaacac agaatggacg gcagacggtc acatagacat gaatatcaag atataccgct    15720
taaaggtgtt atatgatatt gagattatac aagcgactag tcaagcaaca agtagtgaag    15780
aaacacacac ggttaatgat tgcatgtttt acgttcgaca taatgcgagt gggaaatatt    15840
taagcaaaac atttgtgcat tcggggcaat atcgtaatgt taactatgag tttactaatg    15900
```

```
tcagcgatat gaatgtaaaa atgaatgatc aatatgagga aaaattgtac tatgaaggct   15960
attacgttgt acaaggcaaa ggattaagag gattgagggg gtactaatgg gatatttagg   16020
cggttatgaa gatattgaaa atcttacaca gacgggaaat gaaagagagt ttgaaagctc   16080
actagacgga tataacgtgc attttgagca gggtttagat ttattcggta ttggtacacg   16140
tgatgttgaa ttttggtgcc ctaaggctct atattatgct ttacaacgtg aatattctat   16200
attgcacccg ttaagtacag agggttttga agttcccaac ttatggcgca tgtcaaattt   16260
atatcacgga acaaaccaag cgaaagaaat accttggtta aatttgtggg cggaaaaata   16320
cacactggcc gagaacacgt atatttatag caatacatac ctttatttcg caaatgacac   16380
ttctaacatg aaagtagagt tttctatacc taaaacagca actaaaaacg tttctgactg   16440
gtcgagaact caaattaaaa gcggagaaac cccaaacgct aatagaaacg aaaacggatt   16500
aggttttagg tggaaacccc caacaacata tacattcaga tttaaattaa ggttagacgg   16560
cgacattaca gacagctcta tgttccgcac tcaaatagga gagagtggta atgtaaacgt   16620
ggatacaact aaggatataa tggtaaatgg tagacctatg tcttacttca tgcctaacgc   16680
aacaaataca gaaagacctt attgccaaat ccgctgggaa aagatattag gcgataaatt   16740
tgtgaagagg agtcctgtgt ggcatgaatg tgaagtacaa tttactacac ccgccaacgt   16800
ggaaagcgta aaatatcata cgttaaggct tggtgtggga aaaggcacaa aggtaacaat   16860
gttagaacct atgttatatg agggtgaaaa tatcgtcaat cctccattct cattaacacc   16920
acaagaatat tttgagtatg aatatgatag aggtttgcaa ggtcttaagt ttattcagcc   16980
ggctttaggt ttctattaca gcaaagaata tgatttcgca tgtgcttata aagtgaatca   17040
attaaaaggg cttcaagtga ttgattataa tgagagtgtg ggagcattca agatcagatg   17100
tgaggttgat gtatttaaac aaataacaga tgtcacggtt aagtattatg atgataataa   17160
agacgctgtg gcagatacaa gcatgaatat atacaacaca ataggtcaca gtaatgtgat   17220
agataatagt agcggagagg gaaacaacag ctcttacttc ttaaagacta gcggtaaggg   17280
tggaatagtt acaaacttcc atgttaatcc aagcaataag agagtaccct tactttttac   17340
aggacaagta cattctgata catgggattt agaaggatat accaacacat ggggaaataa   17400
gatgtattac tatacaggta acgcaatgga aaacaagaaa gagaattaaa ggggagtata   17460
tgaaagaaat agcattagta ttgtttatgc aggcattggc tttggcaatt gagtttatag   17520
acacaggaac tttaacacct agtgtaaaga aaaggctaag cattgaagct attgtattgc   17580
ttgtatatgt agcaggtaat acagtgttta aaggtatgat aagcacagag ttacttagtc   17640
taattggtac tgtatatatt ggtcttgtat gtgcttcatt gtttaagttc cttaatggaa   17700
tgaaagataa agcagtggac ctaacagact agtagtagta tgtagtagtg tgtagtatat   17760
agtatagtga tacataatgt ataagataat catgattat tttttaaatt gtgattattt    17820
ttttatttaa aattttgtaa gattttgttg aggacattta aggggtgtg tatataaagg     17880 ggtgggtct ctatcaagcc taactcctca aaatccattt ttctaaaatt tgaaattgaa     17940
aagcatatca ccgatgcatt ctctacaagc tccatataag cccgtataag cattttacag   18000
ctcacttcct ataacttatc aagacaataa aaaaacagc ctcacaagcc gttatattag     18060
ctcacaagac tatttatta actctttact ttttccactt ccaagcgtcg tatttatctt     18120
tcaaccaatc ccaagcagta ccaagggcac cccataacgg aatatcaatg aaaatcactg   18180
taataatcac tactactacc gcaagactca taagcaaagc gcagtttacc agtgtttcaa   18240
gtgcggggga tacttcgata gggttgttgt gtgagttgtt attgattaag ctgttccata   18300
```

```
caatgaaatc tgtaatactc attatccatt acatccatat tctttagcga ttgtatcaaa    18360
catgtgttca ttcgcctttg tcatcagttc catttctttt gcgtgccctg caaggtcaat    18420
ttctttgctt tcaatccatt cgggcgtttg catatgttca aggtctgcct ttagtgcatt    18480
agctgcctct agcttttctt tttcatctag gtcatcccaa atgctttcag tcactaataa    18540
caccatacgt ggggtttgtg gcaactcgtt aaggtcaatt actttactaa aattaatact    18600
cattcttaca tttcctccaa catcattttt tcgatttcac ctgcaatatt tacataaccg    18660
ataaacaacc ctttatattg agtaaaagtc aagtcatatg tcagcttgtc agttgcattt    18720
tctggtacat taatttcatc aaggtctagt aaatgtcgtt ctattagttc atcaagcata    18780
ccaagaacga taatagcctc ttgttttcct gcattggcta caacaccaac ggcaacctta    18840
gtagcttgta caccgtcggc aatatcaagg tatgcgttgt tcaatactgg caaagctttt    18900
gtataaaatt tttgtgtaaa tggctctgtt tcaaccaata cctttgcaag ttccatgttt    18960
gtgcgttcgt tgtggtcgtt cgcaatacct ttaattaatt ctaattctgt tgtaaaattc    19020
atagtaaaac ctcttttttc tattctccta aaattgaagc aaacattgca atcatcttag    19080
caccgtcaaa acctgcttcc atgcacccgt gatagttttg ataaaccact tctaaatatt    19140
catgtttaga aaactctctt tgttccaatt gaatatctga attgtgaagc tcttctccca    19200
atgtttcaca catatcaacc caagcggtgt gccattgttt agcattttca tcaaatgaga    19260
taaagttttc gtctaagaac tcttccaagt cgtagaaacg ttcttcaata tcatcaatca    19320
aagcataaag gatttcaatc atttccttgt catatttatc tccttttgcg cttccgtcat    19380
ctggtaagtc gtattttcct aacaagatac cgataaggct gtcatgtggg ttcatttcat    19440
ttgcaatacg ttgcgcaatg tcgttaatag tgattgtttg tgtcataagg ttttaaccct    19500
ttctttattt tatgtattta ttatagatta ttttttaata gatgtcaatt acaagagtgt    19560
tacaattaat taaacttgca tgttagttag tttgttaaga tatgacaagc gtttgtcttt    19620
gtgatactcc aaattattgc cccaacgtgt ttgcaatgtc aattttaaac cctcaataat    19680
gtaattacgc aatataacgt tattgttgat gtcgtcaagc gtgtaattaa gttcttgact    19740
gtactgattg agttctaata cctcattttc agcaaaagcc tccaattctt ctatggtcat    19800
gctgttataa cccgtgctaa atttgataaa tttaaatgtt ttatcgttaa tcataagccc    19860
ccctcataat aatttttagt gtattttccg ttgctgtgtt ctgatgtata gtaaattcat    19920
ctttcaagcc atttacagcc tttctaagca tgtttgaagt gtcgtgtgat acaattatca    19980
tcatttcgat ctctaacgct ctaaacgctt gatatgtgct taaattgccg tttactgcgt    20040
ggatatgctc atgtacatca gcgaaagctg ttcccattgg ctcacgttca tagtcgagtg    20100
acacggtaaa ccctaaatcc tctaggaact gcttaatgtc ctctttagtg ctcatatgaa    20160 ccccctatt tttgcatgtt atagctatca atgagatatt ttaagttgtc tttaaaccat    20220
tgtagcttac cttgtgggct gaaatattgg tgattaggaa cacctttttg aaacataatt    20280
tcgccaatag cttcgctgtt agccactgta tcaaggaaat caaggcttgt tagtaccttg    20340
gcactattaa taatgctgtc agctaggtta ctcaactccg caaacttcat agcttttttca    20400 atcttttctg tttgctcttg gtcatatgcc ataagttcca agtactggta ttggtcgttg    20460
tgacgtctta gcttgcctag cgtatttaat acaatgatgt cagcgatatc tttgtcaagc    20520
acttcatctt cttcccaatt catgcgatac ttcttattag tatttcgcac ataattcttc    20580
aacccttgtt tgatacctag taggctgtga atttgtttaa gtgtagggaa ttcaaggtaa    20640
taaatttctt ctaagcgtgt aaccatttta taaaatctcc tttatttctg tgataaatgt    20700
```

```
ttgtttaaat tcatttatgt gtgccaattc tactaaattt tctctatctt ggcaaaagat   20760
tagagggaca tttatatcaa tccagtgtaa cacttcatca agcggacaat tgtctatcaa   20820
gctcatttta tccactatgt cgagtgcttc gtcataatca tatccatttt taaagcgata   20880
atcaaagtta ataaaaacca tatacaccgc ctttagaatg gtaaatcttc gtcagatact   20940
tccataggcg agccaccaaa taagtcaccc tctggcgctt gtgtagtgaa ttgttgacct   21000
gcatttgagt gattttcacg attaagatta aatagagggg ttacctttgc aaattctgca   21060
ttgagataag tcttgccgtc ttttcttct tttttgatat tgtcaacgaa caccgttaca   21120
taatcgcccc acgttacaac aggtggttgc caaatgttac caatatagcc atcgaatgga   21180
tatgcactga atgagcttac cagtttagca ccttttgcg tttgtacttc acgtgtgttt   21240
ttttcattaa tttggaatgt ttctaaaata atcataggtt taaaatctcc tcttttggtg   21300
taataaattg atgtgaccac tcgggcaagt tatgcgcctg ttcccaactc atatattcta   21360
cagcgtcagg ataatctgtt tttacaatgt cgcccgtttg gttcatgaaa gtaaattat    21420
atactgtgtt cactcccggt aatattacag cgtactgttt gctatcagtt gggataaact   21480
caaactcacc ttttaaatac agtgataaaa tttcacctaa ggcaagctct gaatgctccc   21540
aaatatcgtc aaacaaatcg tttaaattat atgggtcttg gtcgtccttt tgccaataat   21600
agtaagcttg gaatagagag ttgttttag cgactctttc cagtgtttca aaagcttctt    21660
tttcaattt catagttcct tgtagcattt taatcctcca cctcatgtaa ccattcacct   21720
aaccattcgc ccatgtcgtc gatcagttcg tcagcctctt cttttgtcaa aatatcaatc   21780
ttttcgaaat ggtctgtttc ttctaatcct gcattttag taaagtagtg atatttaaat   21840
agccctcgtt ctggcacttg ctcgtgatac aaacggtatt taatttcttt ttgtaaaagc   21900
tccgcttcac ctttgataag tttgatgatg aattcagacg gccacccaa acgctcatca    21960
taaatgaatt gaatgagttg ccagcccatc gttttccacat tagcgtcatg taaccagttc   22020
gctaaatccc gtactagtcc gcgctcgtcg cactctttat aatacttaaa taattctttt   22080
ggtagataga ttttttccat tttttattt tcctcctaaa tcgtcaatca ctagaccttg    22140
cttgaataat tcatttgcgt ggtctgatgt cattgtgcct aagttaatct gttctaagag   22200
ataagatttt ttatacttct taggttgttg cggtgtttgc ttaggttgtg ctttacgttg   22260
ttgttgctta ggtttttgag cgtatccgct agcttggttt gcgtcgtcgt cctcttcact   22320
agtgataccg aataccgtgc taagtgaata gcgtcttgca tatgtgatag cactccctaa   22380
ctgctgtggg tcgtttttag tcggtttcaa ctctaccgca cctagtgaag cccattgtcc   22440
gttttcgtgg aagataacag tacttagctc gtttgcttca atatcttgca agaaacttaa   22500
ccctgtgcct tcaacagctt tctcaacaca atcaacaaca gcctctagag gtacatactt   22560
agagccaaaa taagggtttg ccttgtcttt ctttggctgt actactttag cccgtgcaat   22620
tgttagggct tgaaacaatt cttgtttc ctctgaaatt tcaattact taaactcctt     22680
tgtaaattgt ttgtgacatt ttgtgttatt gcattggtat gttacggcat gtgcataacc   22740
ttgtgcaacc ttaatatttt tagtaccgca atgcgggcat ttaataaact tattaaacat   22800
cccaagcctc cgtaaatttg atgtcaactt tttcttcgct atgctcaaag cgatcgctta   22860
caagcatgga aagaacgtat gccatttccg accatgtagt tgtttcgtca tcgatttctt   22920
taaatgcttc gaacaactct tggttttcta gttttaatga attcttgctt tcaacaaact   22980
ttccaaaatt tatgaaaata gttaagctca tttggtttga aattgtgtca attgtttttt   23040
gcgttagttt cataaggttt tacctctttc tttatttgat atattcatta tacactaatt   23100
```

```
tgtgttacat gtcaatatat aatattttac aattgtgtta ctcttcatta ggtactttaa    23160
agcctttgag ctgtgcagtc tttcttatcc attcttggcg ctcttgctca tgttgtttta    23220
caaagtcttt agagaacgat ttatattgcc cagctttctt acctgtcttg tatttctcac    23280
gcttagggaa gccttttact gtgtaatact ctctacacaa ttcaaaccag ttaaaagcca    23340
tgctataagc ttctagtgtt gtaaatgcgt gatagtttaa actttgctcc ctaaagtcct    23400
taaaatcgtc ccagtctaaa ggaatactca ttttaagacc ccctcgataa acaaggtaaa    23460
tttttcgttc gtctgtccgt tccaagcatg aaaaatgtca acgtaattat taataacagg    23520
gtctagcttt tcatctgaat gccctaattc gtttaagtca gctttgtaat cacgatattt    23580
caccatatca tcttcaaaag tactattctc tttcagccct gcacggattt tatactttac    23640
agcgtttagg aaaaagaaac cctcttccat tgtgtaaata tcacccattt gatttgtttg    23700
ataacgtgac atctgtttca taaagtcacg caattgaaac ccttgtgcgt ttgcataata    23760
atctttagta atcttagtca tttaaaatct atcctccaat attgaattaa ttgtatgctc    23820
aacggcttct tcgtccattt tgagcgtatc cattgcatat cttgatataa cacctaacat    23880
catatccaac ttacctaaag gcttgtacaa taactccgca caatcgtata ttgtcgcgcc    23940
gtcttgctca agttttctta gtaagtcgac cccgataggg tcagcgtctt ttgttatttc    24000
cgaaccgtct gaaaagtgat acgttatttc agttatcttc tttccttctg gtataaccca    24060
gttttcattc ttccgatcta tactcgctca actcctcatc taattctcta agctcatttt    24120
ctaaactttc aatctcgtcc caagcttcat caagtctgca ttcaaggttt tcgttttcct    24180
ctcggagttc ttccaactct gcttcaagct cttcaatttc tgcattcttg tctttgatca    24240
tttcgttaag ttcttcgatc ttttcacgac cttcctcaac tgttctaact accatttaat    24300
tttcctccaa tttataaact ttgtattttc cttcttgtgg tcgttttgac cgtttacgct    24360
tgctatcctt tgcta                                                     24375
```

LACTOCOCCUS GARVIEAE BACTERIOPHAGE LAC-GAP-3 AND USE THEREOF IN INHIBITING PROLIFERATION OF LACTOCOCCUS GARVIEAE BACTERIA

CROSS-REFERENCE TO RELATED APPLICATIONS

This application is a U.S. National Phase Application of International Application No. PCT/KR2017/009077, filed Aug. 21, 2017, which claims priority to Korean Application No. 10-2016-0114167, filed Sep. 6, 2016, each of which are hereby incorporated by reference in their entirety.

REFERENCE TO SEQUENCE LISTING

The Sequence Listing submitted Sep. 25, 2019 as a text file named "08162_0050U1_Revised_Sequence_Listing.txt," created on Sep. 18, 2019, and having a size of 31,636 bytes is hereby incorporated by reference pursuant to 37 C.F.R. § 1.52(e)(5).

TECHNICAL FIELD

The present invention relates to a bacteriophage isolated from nature, which infects *Lactococcus garvieae* to thus kill *Lactococcus garvieae*, and a method for preventing and treating a *Lactococcus garvieae* infection using a composition including the same as an active ingredient. More particularly, the present invention relates to a Siphoviridae bacteriophage Lac-GAP-3 (Accession number: KCTC 12816BP) isolated from nature, which has the ability to specifically kill *Lactococcus garvieae* and which includes a genome expressed by SEQ. ID. NO: 1, and a method for preventing a *Lactococcus garvieae* infection and a treatment method after the *Lactococcus garvieae* infection using a composition including the bacteriophage as an active ingredient.

BACKGROUND ART

*Lactococcus garvieae*, one of the causative agents of fish streptococcosis, is a gram-positive, and has a chain shape. *Lactococcus garvieae*, is known as a representative fish pathogenic bacterium that mostly infects internal organs of fishes such as olive flounder, sweet fish, tilapia, rainbow trout, yellow tail, sardine, and sea bream to thus cause hemorrhaging, resulting in streptococcosis. Two serotypes, including a KG− type and a KG+ type, are known serotypes of *Lactococcus garvieae*, depending on the presence or absence of a capsular antigen (K). Most *Lactococcus garvieae* isolated from aquaculture sites is the KG− type having a capsule, which is generally more toxic than the KG+ type having no capsule.

The symptoms of streptococcosis of fish infected with *Lactococcus garvieae* are as follows. Individuals infected with streptococcosis float passively or lie still on the bottom of the water tank and perform a swinging motion. Further, the individuals have exophthalmos or petechial hemorrhages inside the gill lid, and congestion is observed in the chest and ventral fins. Anatomical findings include brain damage, and moreover, darkening of the body, rubefaction of the mouth, exophthalmos, corneal clouding, liver congestion, ascites, and hernia may occur.

*Lactococcus garvieae* causes serious economic damage in the aquaculture industry by causing streptococcosis in various fishes. In particular, the outbreak of streptococcosis in fish caused by a *Lactococcus garvieae* infection occurs frequently, resulting in great economic damage. Therefore, there is an urgent need to develop a method that is applicable for preventing and further treating a *Lactococcus garvieae* infection.

Antibiotics are extensively used for the inhibition and treatment of infections caused by *Lactococcus garvieae*. Recently, the effectiveness of antibiotics has been continuously decreasing due to the increase of antibiotic-resistant bacteria, and the development of effective methods other than antibiotics is required due to the increased number of regulations on the use of antibiotics in cultured fish. Especially, there is a great demand for environmentally friendly methods.

Recently, the use of bacteriophages as a countermeasure against bacterial diseases has attracted considerable attention. In particular, interest in bacteriophages is higher than ever due to the preference of environmentally friendly methods. Bacteriophages are very small microorganisms infecting bacteria and are usually simply called "phages". Once a bacteriophage infects bacteria, the bacteriophage is proliferated in the inside of the bacterial cell. After proliferation, the progeny of the bacteriophage destroys the bacterial cell wall and escapes from bacteria as the host, suggesting that the bacteriophage has the ability to kill bacteria.

The manner in which the bacteriophage infects bacteria is characterized by very high specificity thereof, so that the number of types of bacteriophages infecting a specific bacterium is limited. That is, a certain bacteriophage can infect only a specific bacterium, suggesting that a certain bacteriophage can kill only a specific bacterium and cannot harm other bacteria. Due to this bacteria specificity of bacteriophages, the bacteriophage confers antibacterial effects only upon target bacteria and does not affect commensal bacteria in the environment or in the intestines of fish. Conventional antibiotics, which have been widely used for bacterial treatment, influence many kinds of bacteria coincidentally. This causes problems such as environmental pollution or the disturbance of normal flora in animals. On the other hand, the use of bacteriophages does not disturb normal flora in animals, because the target bacterium is killed selectively. Hence, the bacteriophage may be utilized safely, which thus greatly lessens the probability of adverse actions in use compared to any other conventional antibiotics.

Bacteriophages were first discovered by the English bacteriologist Twort in 1915 when he noticed that *Micrococcus* colonies melted and became transparent by something unknown. In 1917, the French bacteriologist d'Herelle discovered that *Shigella dysenteriae* in the filtrate of dysentery patient feces was melted by something, and further studied this phenomenon. As a result, he identified bacteriophages independently, and named them bacteriophages, which means "to eat bacteria". Since then, bacteriophages acting against such pathogenic bacteria as *Shigella, Salmonella Typhi*, and *Vibrio cholerae* have been continuously identified.

Owing to the unique ability of bacteriophages to kill bacteria, bacteriophages have attracted anticipation as an effective countermeasure against bacterial infection since their discovery, and there has been a lot of research related thereto. However, since penicillin was discovered by Fleming, studies on bacteriophages have continued only in some Eastern European countries and the former Soviet Union because the spread of antibiotics was generalized. Since 2000, the limitations of conventional antibiotics have appeared due to the increase in antibiotic-resistant bacteria, and the possibility of developing bacteriophages as a substitute for conventional antibiotics has been highlighted, so that bacteriophages are again attracting attention as antibacterial agents. In particular, recently, government regulations for the use of antibiotics have become more stringent around the world, and thus interest in bacteriophages is increasing and industrial applications therefor are increasingly arising.

As demonstrated above, bacteriophages tend to be highly specific for bacteria. Because of this specificity, bacteriophages frequently exhibit an antibacterial effect only for certain strains of bacteria, even though the bacteria belong to the same species. In addition, the different bacteriophages exhibit different antibacterial strengths against the same bacteria strain. Therefore, it is necessary to collect many kinds of bacteriophages that are useful to control specific bacteria efficiently. Hence, in order to develop the effective bacteriophage utilization method in response to *Lactococcus garvieae*, many kinds of bacteriophages that exhibit antibacterial action against *Lactococcus garvieae* must be acquired. Furthermore, the resulting bacteriophages need to be screened as to whether or not they are superior to others from the aspect of antibacterial strength and spectrum.

DISCLOSURE

Technical Problem

Therefore, the present inventors endeavored to develop a composition applicable for the prevention or treatment of a *Lactococcus garvieae* infection using a bacteriophage that is isolated from nature and can selectively kill *Lactococcus garvieae*, and further to establish a method for preventing or treating a *Lactococcus garvieae* infection using the composition. As a result, the present inventors isolated a bacteriophage suitable for this purpose from nature and secured the gene sequence of the genome that distinguishes the isolated bacteriophage from other bacteriophages. Then, the present inventors developed a composition including the bacteriophage as an active ingredient, and identified that this composition could be efficiently used to prevent and treat a *Lactococcus garvieae* infection, leading to the completion of the present invention.

It is an object of the present invention to provide a Siphoviridae bacteriophage Lac-GAP-3 (Accession NO: KCTC 12816BP), deposited under the Budapest Treaty on the International Procedure at the Korean Collection for Type Cultures, Korea Research Institute of Bioscience and Biotechnology (KRIBB), 125 Gwahak-ro, Yuseong-gu, Daijeon 305-806, Republic of Korea; the deposit was made on May 20, 2015) isolated from nature, which as the ability to specifically kill *Lactococcus garvieae* and which includes the genome expressed by SEQ. ID. NO: 1.

It is another object of the present invention to provide a composition applicable for preventing *Lactococcus garvieae* infection, which includes a bacteriophage Lac-GAP-3 infecting *Lactococcus garvieae* to thus kill *Lactococcus garvieae* as an active ingredient, and a method for preventing a *Lactococcus garvieae* infection using said composition.

It is another object of the present invention to provide a composition applicable for treating a *Lactococcus garvieae* infection, which includes a bacteriophage Lac-GAP-3 infecting *Lactococcus garvieae* to thus kill *Lactococcus garvieae* as an active ingredient, and a method for treating a *Lactococcus garvieae* infection using said composition.

It is another object of the present invention to provide a medicine bath agent (immersion agent) for preventing and treating a *Lactococcus garvieae* infection using said composition.

It is another object of the present invention to provide a feed additive effective upon farming by preventing and treating a *Lactococcus garvieae* infection using said composition.

Technical Solution

The present invention provides a Siphoviridae bacteriophage Lac-GAP-3 (Accession number: KCTC 12816BP) isolated from nature, which has the ability to specifically kill *Lactococcus garvieae* and which includes a genome expressed by SEQ. ID. NO: 1, and a method for preventing and treating *Lactococcus garvieae* infection using a composition including the same as an active ingredient.

The bacteriophage Lac-GAP-3 was isolated by the present inventors and then deposited at Korean Collection for Type Cultures, Korea Research Institute of Bioscience and Biotechnology on May 20, 2015 (Accession number: KCTC 12816BP).

The present invention also provides a medicine bath agent and a feed additive applicable for the prevention or treatment of a *Lactococcus garvieae* infection, which include the bacteriophage Lac-GAP-3 as an active ingredient.

Since the bacteriophage Lac-GAP-3 included in the composition of the present invention kills *Lactococcus garvieae* efficiently, it is regarded effective in the prevention (prevention of infection) or treatment (treatment of infection) of diseases caused by *Lactococcus garvieae*. Therefore, the composition of the present invention can be utilized for the prevention and treatment of diseases caused by *Lactococcus garvieae*.

In this description, the term "prevention" or "prevent" indicates (i) to block a *Lactococcus garvieae* infection; and (ii) to inhibit the development of diseases caused by a *Lactococcus garvieae* infection.

In this description, the term "treatment" or "treat" indicates all actions that (i) suppress diseases caused by *Lactococcus garvieae*; and (ii) alleviate the pathological condition of the diseases caused by *Lactococcus garvieae*.

In this description, the term "isolate", "isolating", or "isolated" indicates actions which isolate bacteriophages from nature by applying diverse experimental techniques and which secure characteristics that can distinguish the target bacteriophage from others, and further includes the action of proliferating the target bacteriophage using bioengineering techniques so that the target bacteriophage is industrially applicable.

The pharmaceutically acceptable carrier included in the composition of the present invention is one that is generally used for the preparation of a pharmaceutical formulation, and examples thereof include lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methylcellulose, methylhydroxybenzoate, propylhydroxybenzoate, talc, magnesium stearate, and mineral oil, but are not limited thereto. The composition of the present invention may additionally include lubricants, wetting agents, sweeteners, flavors, emulsifiers, suspending agents, and preservatives, in addition to the above ingredients.

In the composition of the present invention, the bacteriophage Lac-GAP-3 is included as an active ingredient. The bacteriophage Lac-GAP-3 is included at a concentration of $1×10^1$ pfu/ml to $1×10^{30}$ pfu/ml or $1×10^1$ pfu/g to $1×10^{30}$ pfu/g, and preferably at a concentration of $1×10^4$ pfu/ml to $1×10^{15}$ pfu/ml or $1×10^4$ pfu/g to $1×10^{15}$ pfu/g.

The composition of the present invention can be formulated according to a method that can be easily performed by those of ordinary skill in the art to which the present invention pertains using a pharmaceutically acceptable carrier and/or excipient in the form of a unit dose or in a multi-dose container. The formulation may be in the form of a solution, suspension, or emulsion in oil or a water-soluble medium, extract, powder, granule, tablet, or capsule. A dispersing agent or stabilizer may be additionally included.

The composition of the present invention may be prepared as a medicine bath agent and a feed additive according to the purpose of use, without limitation thereto.

For this purpose, bacteriophages that confer antibacterial activity against other bacterial species may be further included in the composition of the present invention in order to improve the effectiveness thereof. In addition, other kinds of bacteriophages that have antibacterial activity against *Lactococcus garvieae* may be further included in the composition of the present invention. These bacteriophages may be combined properly so as to maximize antibacterial effects, because their antibacterial activities against *Lactococcus garvieae* may be different from the aspects of antibacterial strength and spectrum.

Advantageous Effects

The method for preventing and treating *Lactococcus garvieae* infection using the composition including the bacteriophage Lac-GAP-3 as an active ingredient according to the present invention may have the advantage of very high specificity for *Lactococcus garvieae*, compared with the conventional methods based on chemical materials including conventional antibiotics. This means that the composition can be used for preventing or treating the *Lactococcus garvieae* infection without affecting other commensal bacteria that are useful and has fewer side effects according to the use thereof. In general, when chemical materials such as antibiotics are used, commensal bacteria are also damaged, thus weakening immunity in animals and entailing various side effects owing to the use thereof.

Further, the composition of the present invention uses a bacteriophage isolated from nature as an active ingredient, and thus it is very environmentally friendly.

Meanwhile, in the case of bacteriophages exhibiting antibacterial activity against the same species of bacteria, the antibacterial activities of the bacteriophages are different with regard to antibacterial strength and spectrum [the spectrum of the antibacterial activity of the bacteriophages applied to individual bacteria strains in terms of the strains of various bacteria belonging to *Lactococcus garvieae*. Typically, bacteriophages are usually effective only on some bacterial strains, even within the same species. That is to say, the antibacterial activity of bacteriophage may depend on the bacterial strain even for the same species of bacteria]. Accordingly, the present invention may provide antibacterial activity against *Lactococcus garvieae* different to that provided by other bacteriophages acting on *Lactococcus garvieae*. This provides significantly different applicability to industrial fields.

MODE FOR INVENTION

Hereinafter, the present invention will be described in more detail with reference to Examples. However, the Examples are merely examples of the present invention, and the scope of the present invention is not limited to the Examples.

Example 1: Isolation of Bacteriophage Capable of Killing *Lactococcus garvieae*

Samples were collected from nature to isolate the bacteriophage capable of killing *Lactococcus garvieae*. Meanwhile, the *Lactococcus garvieae* used for the bacteriophage isolation was purchased from the Korea Environmental Microorganisms Bank (Accession number: KEMB 2221-072).

The isolation procedure of the bacteriophage is described in detail hereinafter. The collected sample was added to a TSB (Tryptic Soy Broth) culture medium (casein digest, 17 g/L; soybean digest, 3 g/L; dextrose, 2.5 g/L; NaCl, 5 g/L; dipotassium phosphate, 2.5 g/L) inoculated with *Lactococcus garvieae* at a ratio of 1/1,000, followed by shaking culture at 30° C. for 3 to 4 hours. Upon completion of the culture, centrifugation was performed at 8,000 rpm for 20 minutes and a supernatant was recovered. The recovered supernatant was inoculated with *Lactococcus garvieae* at a ratio of 1/1,000, followed by shaking culture at 30° C. for 3 to 4 hours. When the sample contained the bacteriophage, the above procedure was repeated a total of 5 times in order to sufficiently increase the number (titer) of bacteriophages. After repeating the procedure 5 times, the culture solution was subjected to centrifugation at 8,000 rpm for 20 minutes. After the centrifugation, the recovered supernatant was filtered using a 0.45 μm filter. The obtained filtrate was used in a typical spot assay for examining whether or not a bacteriophage capable of killing *Lactococcus garvieae* was included therein.

The spot assay was performed as follows: TSB culture medium was inoculated with *Lactococcus garvieae* at a ratio of 1/1,000, followed by shaking culture at 30° C. overnight. 3 ml (OD600 of 1.5) of the culture solution of *Lactococcus garvieae* prepared as described above was spread on TSA (Tryptic Soy Agar: casein digest, 15 g/L; soybean digest, 5 g/L; NaCl, 5 g/L; agar, 15 g/L) plate. The plate was left on a clean bench for about 30 minutes to dry the spread solution. After drying, 10 μl of the prepared filtrate was spotted onto the plate which *Lactococcus garvieae* was spread and then left for about 30 minutes to dry. After drying, the plate that was subjected to spotting was standing-cultured at 30° C. for one day, and then examined for the formation of a clear zone at the position at which the filtrate was dropped. In the case of the filtrate generating the clear zone, it is judged that the bacteriophage capable of killing *Lactococcus garvieae* is included therein. Through the above examination, the filtrate containing the bacteriophage having the ability to kill *Lactococcus garvieae* could be obtained.

Figure 1:
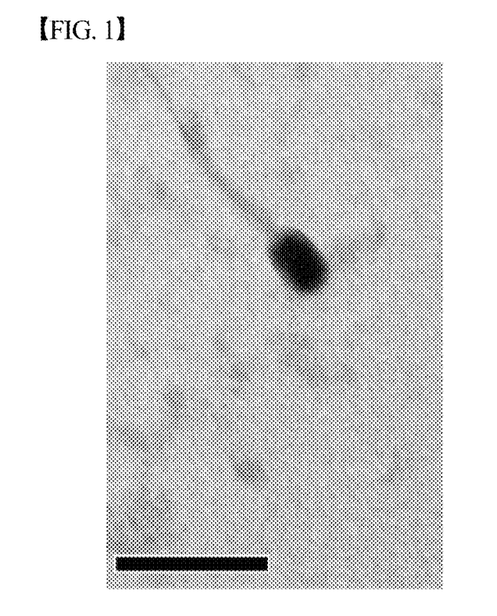
FIG. 1 is an electron micrograph showing the morphology of the bacteriophage Lac-GAP-3.

The pure bacteriophage was isolated from the filtrate confirmed above to have the bacteriophage capable of killing *Lactococcus garvieae*. A conventional plaque assay was used for the isolation of the pure bacteriophage. In detail, a plaque formed in the course of the plaque assay was recovered using a sterilized tip, which was then added to the culture solution of *Lactococcus garvieae*, followed by culturing at 30° C. for 4 to 5 hours. After the culturing, centrifugation was performed at 8,000 rpm for 20 minutes to obtain a supernatant. The *Lactococcus garvieae* culture solution was added to the obtained supernatant at a volume ratio of 1/50, followed by culturing at 30° C. for 4 to 5 hours. In order to increase the number of bacteriophages, the above procedure was repeated at least 5 times. Then, centrifugation was performed at 8,000 rpm for 20 minutes to obtain the final supernatant. A plaque assay was further performed using the resulting supernatant. In general, the isolation of a pure bacteriophage is not completed through a single iteration of a procedure, so the above procedure was repeated using the resulting plaque formed above. After at least 5 repetitions of the procedure, the solution containing the pure bacteriophage was obtained. The procedure for the isolation of the pure bacteriophage was generally repeated until the generated plaques became similar to each other in size and morphology. In addition, the final isolation of the pure bacteriophage was confirmed using electron microscopy. Until the isolation of the pure bacteriophage was confirmed using the electron microscopy, the above procedure was repeated. The electron microscopy was performed according to a conventional method. Briefly, the solution containing the pure bacteriophage was loaded on a copper grid, followed by negative staining with 2% uranyl acetate and drying. The morphology thereof was then observed using a transmission electron microscope. The electron micrograph of the pure bacteriophage that was isolated is shown in FIG. 1. Based on the morphological characteristics, the novel bacteriophage above was confirmed to belong to the Siphoviridae bacteriophage.

The solution containing the pure bacteriophage confirmed above was subjected to the following purification process. The *Lactococcus garvieae* culture solution was added to the solution containing the pure bacteriophage at a volume ratio of 1/50 based on the total volume of the bacteriophage solution, followed by further culturing for 4 to 5 hours. After the culturing, centrifugation was performed at 8,000 rpm for 20 minutes to obtain a supernatant. This procedure was repeated a total of 5 times to obtain a solution containing sufficient numbers of the bacteriophage. The supernatant obtained from the final centrifugation was filtered using a 0.45 μm filter, followed by a conventional polyethylene glycol (PEG) precipitation process. Specifically, PEG and NaCl were added to 100 ml of the filtrate until reaching 10% PEG 8000/0.5 M NaCl, and then left at 4° C. for 2 to 3 hours. Thereafter, centrifugation was performed at 8,000 rpm for 30 minutes to obtain the bacteriophage precipitate. The resulting bacteriophage precipitate was suspended in 5 ml of a buffer (10 mM Tris-HCl, 10 mM $MgSO_4$, 0.1% Gelatin, pH 8.0). The resulting material was referred to as a bacteriophage suspension or bacteriophage solution.

As a result, the pure bacteriophage purified above was collected, was named the bacteriophage Lac-GAP-3, and was then deposited at Korean Collection for Type Cultures, Korea Research Institute of Bioscience and Biotechnology on May 20, 2015 (Accession number: KCTC 12816BP).

Example 2: Separation and Sequence Analysis of Genome of Bacteriophage Lac-GAP-3

The genome of the bacteriophage Lac-GAP-3 was separated as follows. The genome was separated from the bacteriophage suspension obtained using the same method as in Example 1. First, in order to eliminate DNA and RNA of *Lactococcus garvieae* included in the suspension, 200 U of each of DNase I and RNase A was added to 10 ml of the bacteriophage suspension and then left at 37° C. for 30 minutes. After being left for 30 minutes, in order to inactivate the DNase I and RNase A activity, 500 μl of 0.5 M ethylenediaminetetraacetic acid (EDTA) was added thereto and then left for 10 minutes. In addition, the resulting mixture was further left at 65° C. for 10 minutes, and 100 μl of proteinase K (20 mg/ml) was then added thereto so as to break the outer wall of the bacteriophage, followed by reaction at 37° C. for 20 minutes. After that, 500 μl of 10% sodium dodecyl sulfate (SDS) was added thereto, followed by reaction at 65° C. for 1 hour. After the reaction for 1 hour, 10 ml of the solution of phenol:chloroform:isoamyl alcohol mixed at a component ratio of 25:24:1 was added to the reaction solution, followed by mixing well. In addition, the resulting mixture was subjected to centrifugation at 13,000 rpm for 15 minutes to separate layers. Among the separated layers, the upper layer was selected, and isopropyl alcohol was added thereto at a volume ratio of 1.5, followed by centrifugation at 13,000 rpm for 10 minutes to precipitate the genome. After collecting the precipitate, 70% ethanol was added to the precipitate, followed by centrifugation at 13,000 rpm for 10 minutes to wash the precipitate. The washed precipitate was recovered, vacuum-dried and then dissolved in 100 μl of water. This procedure was repeated to obtain a sufficient amount of the genome of the bacteriophage Lac-GAP-3.

Next-generation sequencing analysis using Illumina Mi-Seq equipment from Macrogen, Inc. was performed, and information on the sequence of the genome of the bacteriophage Lac-GAP-3 obtained above was then secured. The finally analyzed genome of the bacteriophage Lac-GAP-3 had a size of 24,375 bp and the sequence of the whole genome was expressed by SEQ. ID. NO: 1.

The homology (similarity) of the bacteriophage Lac-GAP-3 genomic sequence obtained above with previously reported bacteriophage genomic sequences was investigated using BLAST on the web. As a result of the BLAST investigation, bacteriophage sequences with homology of 50% or more were not confirmed.

Based upon this result, it is concluded that the bacteriophage Lac-GAP-3 must be a novel bacteriophage that has not been reported previously. Further, since the antibacterial strength and spectrum of bacteriophages typically depend on the type of bacteriophage, it is considered that the bacteriophage Lac-GAP-3 can provide antibacterial activity different from that of any other bacteriophages reported previously.

Example 3: Investigation of Ability of Bacteriophage Lac-GAP-3 to Kill *Lactococcus garvieae*

Figure 2:
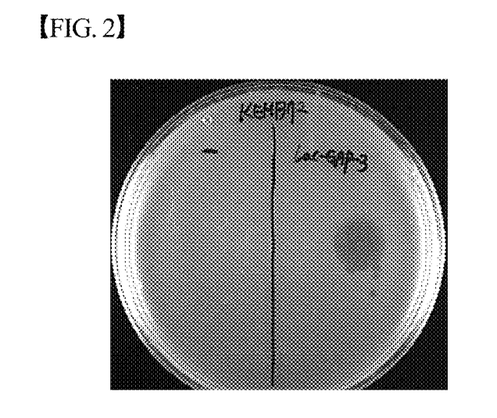
FIG. 2 is a photograph showing the results of an experiment on the ability of the bacteriophage Lac-GAP-3 to kill *Lactococcus garvieae*. Based on the center line of the plate culture medium, only the buffer containing no bacteriophage Lac-GAP-3 is spotted on the left side thereof, and the solution containing bacteriophage Lac-GAP-3 is spotted on the right side thereof. The clear zone observed on the right side is a plaque formed by lysis of the target bacteria due to the action of bacteriophage Lac-GAP-3.

The ability of the isolated bacteriophage Lac-GAP-3 to kill *Lactococcus garvieae* was investigated. In order to investigate the killing ability, the formation of clear zones was observed using the spot assay in the same manner as described in Example 1. A total of 15 strains which had been isolated and identified as *Lactococcus garvieae* by the present inventors were used as *Lactococcus garvieae* for the investigation of killing ability. The bacteriophage Lac-GAP-3 had the ability to kill a total of 13 strains among 15 strains of *Lactococcus garvieae* as the experimental target. The representative experimental result is shown in FIG. 2. Meanwhile, the ability of the bacteriophage Lac-GAP-3 to kill *Edwardsiella tarda, Vibrio parahaemolyticus, Vibrio anguillarum, Streptococcus iniae, Streptococcus parauberis*, and *Aeromonas salmonicida* was also investigated in a separate experiment. As a result, the bacteriophage Lac-GAP-3 did not have the ability to kill these microorganisms.

Therefore, it is confirmed that the bacteriophage Lac-GAP-3 has the specific ability to kill *Lactococcus garvieae* and a broad antibacterial spectrum against *Lactococcus garvieae*, suggesting that the bacteriophage Lac-GAP-3 can be used as an active ingredient of the composition for preventing and treating *Lactococcus garvieae* infection.

Example 4: Experimental Example Regarding Prevention of *Lactococcus garvieae* Infection Using Bacteriophage Lac-GAP-3

100 μl of a bacteriophage Lac-GAP-3 solution at a level of $1\times10^8$ pfu/ml was added to a tube containing 9 ml of a TSB culture medium. To another tube containing 9 ml of a TSB culture medium, only the same amount of TSB culture medium was further added. A *Lactococcus garvieae* culture solution was then added to each tube so that absorbance reached about 0.5 at 600 nm. After *Lactococcus garvieae* was added, the tubes were transferred to an incubator at 30° C., followed by shaking culture, during which the growth of *Lactococcus garvieae* was observed. As presented in Table 1, it was observed that the growth of *Lactococcus garvieae* was inhibited in the tube to which the bacteriophage Lac-GAP-3 solution was added, while the growth of *Lactococcus garvieae* was not inhibited in the tube to which the bacteriophage solution was not added.

TABLE 1

Growth inhibition of *Lactococcus garvieae*

| Classification | $OD_{600}$ absorbance value | | |
|---|---|---|---|
| | 0 minutes after culture | 60 minutes after culture | 120 minutes after culture |
| Bacteriophage solution is not added | 0.498 | 0.992 | 1.364 |
| Bacteriophage solution is added | 0.498 | 0.294 | 0.168 |

The above results indicate that the bacteriophage Lac-GAP-3 of the present invention not only inhibits the growth of *Lactococcus garvieae* but also has the ability to kill *Lactococcus garvieae*. Therefore, it is concluded that the bacteriophage Lac-GAP-3 can be used as an active ingredient of the composition for preventing a *Lactococcus garvieae* infection.

Example 5: Animal Experiment on Prevention of *Lactococcus garvieae* Infection Using Bacteriophage Lac-GAP-3

The preventive effect of the bacteriophage Lac-GAP-3 on olive flounder subjected to *Lactococcus garvieae* infection was investigated. A total of 2 groups of fifty juvenile olive flounder per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. Over the whole experimental period from the $1^{st}$ day of the experiment, olive flounder in an experimental group (the group to which the bacteriophage was administered) was fed with a feed containing the bacteriophage Lac-GAP-3 at $1\times10^8$ pfu/g according to a conventional feeding method. In contrast, olive flounder in a control group (the group to which the bacteriophage was not administered) was fed with the same feed as in the experimental group except that the bacteriophage Lac-GAP-3 was not contained according to the same method as in the experimental group. From the seventh day after the experiment started, the feed to be provided was contaminated with *Lactococcus garvieae* at a level of $1\times10^8$ cfu/g for two days and thereafter provided respectively twice a day so as to induce a *Lactococcus garvieae* infection. From the ninth day after the experiment started (the second day after the *Lactococcus garvieae* infection was induced), streptococcosis pathogenesis was examined in all test animals on a daily basis. The streptococcosis pathogenesis was examined by measuring a body darkening index. The measurement of the body darkening index was performed using a conventional method for measuring a dark coloration (DC) score (0: normal, 1: slight darkening, 2: strong darkening). The results are shown in Table 2.

TABLE 2

Result of measurement of body darkening index (mean)

| Days | DC score (mean) | | | | | |
|---|---|---|---|---|---|---|
| | D 9 | D 10 | D 11 | D 12 | D 13 | D 14 |
| Control group (bacteriophage is not administered) | 0.80 | 0.80 | 0.76 | 1.04 | 1.08 | 1.12 |
| Experimental group (bacteriophage is administered) | 0.24 | 0.12 | 0.04 | 0.04 | 0 | 0 |

From the above results, it is confirmed that the bacteriophage Lac-GAP-3 of the present invention could be very effective in inhibiting *Lactococcus garvieae* infection.

Example 6: Example of Treatment of Infectious Diseases of *Lactococcus garvieae* Using Bacteriophage Lac-GAP-3

The treatment effect of the bacteriophage Lac-GAP-3 on olive flounder suffering from streptococcosis caused by *Lactococcus garvieae* was investigated. A total of 2 groups of eighty juvenile olive flounder per group (body weight: 5 to 7 g and body length: 8 to 10 cm) was prepared and farmed separately in water tanks, and an experiment was performed for 14 days. The environment surrounding the water tanks was controlled, and the temperature in the laboratory where the water tanks were located was maintained constant. From the fifth day after the experiment started, the feed contaminated with *Lactococcus garvieae* at a level of $1\times10^8$ cfu/g was provided twice a day for three days according to a conventional feeding method. Olive flounder subjects showing clinical symptoms of streptococcosis were observed in both water tanks from the last day of the procedure in which the feed contaminated with *Lactococcus garvieae* was provided. From the next day after the feed contaminated with *Lactococcus garvieae* was provided for three days (the eighth day after the experiment started), olive flounder in an experimental group (the group to which the bacteriophage was administered) was fed with a feed containing the bacteriophage Lac-GAP-3 ($1\times10^8$ pfu/g) according to a conventional feeding method. In contrast, olive flounder in a control group (the group to which the bacteriophage was not administered) was fed with the same feed as in the experimental group except that the bacteriophage Lac-GAP-3 was not contained according to the same method as in the experimental group. From the third day after the forced infection of *Lactococcus garvieae* (the eighth day after the experiment started), streptococcosis pathogenesis was examined in all test animals on a daily basis. The streptococcosis pathogenesis caused by *Lactococcus garvieae* was examined by measuring a body darkening index as in Example 5. The results are shown in Table 3.

TABLE 3

Result of measurement of body darkening index (mean)

| Days | \multicolumn{7}{c}{DC score (mean)} | | | | | | |
|---|---|---|---|---|---|---|---|
| | D 8 | D 9 | D 10 | D 11 | D 12 | D 13 | D 14 |
| Control group (bacteriophage is not administered) | 0.85 | 0.93 | 1.03 | 1.13 | 1.23 | 1.20 | 1.30 |
| Experimental group (bacteriophage is administered) | 0.90 | 0.78 | 0.75 | 0.73 | 0.43 | 0.20 | 0.13 |

From the above results, it is confirmed that the bacteriophage Lac-GAP-3 of the present invention could be very effective in the treatment of infectious diseases caused by *Lactococcus garvieae*.

Example 7: Preparation of Feed Additives and Feeds

Feed additives were prepared using a bacteriophage Lac-GAP-3 solution so that a bacteriophage Lac-GAP-3 was contained in an amount of $1\times10^8$ pfu per 1 g of the feed additives. The method of preparing the feed additives was as follows: Maltodextrin (50%, w/v) was added to the bacteriophage solution and the resulting mixture was then freeze-dried. Finally, the dried mixture was ground into fine powders. In the above-described preparation procedure, the drying procedure can be replaced with drying under a reduced pressure, drying with heat, or drying at room temperature. In order to prepare the control for comparison, the feed additive that did not contain the bacteriophage but contained a buffer (10 mM Tris-HCl, 10 mM $MgSO_4$, 0.1% Gelatin, pH 8.0) used to prepare the bacteriophage solution was prepared.

The two kinds of feed additives that were prepared above were each mixed with a raw fish-based moist pellet at a weight ratio of 250, thus preparing two kinds of final feeds.

Example 8: Preparation of Medicine Bath Agent

The method of preparing a medicine bath agent was as follows: The medicine bath agent was prepared using a bacteriophage Lac-GAP-3 solution so that a bacteriophage Lac-GAP-3 was contained in an amount of $1\times10^8$ pfu per 1 ml of the medicine bath agent. In the method of preparing the medicine bath agent, the bacteriophage Lac-GAP-3 solution was added so that the bacteriophage Lac-GAP-3 was contained in an amount of $1\times10^8$ pfu per 1 ml of a buffer used to prepare the bacteriophage solution, and mixing was sufficiently performed. In order to prepare the control for comparison, the buffer used to prepare the bacteriophage solution was used as the medicine bath agent that did not contain the bacteriophage.

The two prepared kinds of medicine bath agents were diluted with water at a volume ratio of 1,000, resulting in the final medicine bath agent.

Example 9: Confirmation of Feeding Effect on Olive Flounder Farming

Improvement in the feeding result upon olive flounder farming was investigated using the feed and the medicine bath agents prepared in Examples 7 and 8. In particular, the investigation was focused on mortality. A total of 800 juvenile olive flounder was divided into two groups, each including 400 olive flounder (group A; fed with the feed and group B; treated with the medicine bath agent), and an experiment was performed for four weeks. Each group was divided into sub-groups each including 200 olive flounder, and the sub-groups were classified into a sub-group to which the bacteriophage Lac-GAP-3 was applied (sub-group-①) and a sub-group to which the bacteriophage was not applied (sub-group-②). In the present experiment, the target olive flounder was the juvenile (body weight: 5 to 7 g and body length: 8 to 10 cm), and the juvenile olive flounder of the experimental sub-groups were farmed in separate water tanks placed apart from each other at a certain space interval. The sub-groups were classified and named as shown in Table 4.

TABLE 4

Sub-group classification and expression in olive flounder feeding experiment

| | Sub-group classification and expression | |
|---|---|---|
| Application | Bacteriophage Lac-GAP-3 is applied | Bacteriophage is not applied |
| Group fed with feed | A-① | A-② |
| Group treated with medicine bath agent | B-① | B-② |

In the case of provision of the feeds, the feeds prepared in Example 7 were provided according to a conventional feeding method as classified in Table 4. The treatment using the medicine bath agent was performed according to a conventional treatment method using a medicine bath agent as classified in Table 4 using the medicine bath agent prepared as described in Example 8. The results are shown in Table 5.

TABLE 5

Mortality of olive flounder in feeding experiment

| Group | Dead olive flounder/total olive flounder of experiment (No.) | Mortality (%) |
|---|---|---|
| A-① | 6/200 | 3.0 |
| A-② | 41/200 | 20.5 |
| B-① | 9/200 | 4.5 |
| B-② | 53/200 | 26.5 |

The above results indicate that the provision of the feed prepared according to the present invention and the treatment using the medicine bath agent prepared according to the present invention were effective in improving the feeding result in the farming of olive flounder. Therefore, it is concluded that the composition of the present invention could be efficiently applied to improving the results of animal feeding.

While the present invention has been particularly shown and described with reference to exemplary embodiments thereof, those skilled in the art will appreciate that the specific description is only a preferred embodiment, and that the scope of the present invention is not limited thereto. It is therefore intended that the scope of the present invention be defined by the claims appended hereto and their equivalents.

Name of Depositary Authority: Korea Research Institute of Bioscience and Biotechnology Accession number: KCTC 12816BP Accession date: 20150520

The invention claimed is:

1. A method for treating a *Lactococcus garvieae* infection, the method comprising:

administering to an animal other than a human the composition including the Siphoviridae bacteriophage Lac-GAP-3 (Accession number: KCTC 12816BP) which has an ability to specifically kill *Lactococcus garvieae* and which includes a genome expressed by SEQ. ID. NO: 1 as an active ingredient.

2. The method for treating the *Lactococcus garvieae* infection of claim 1, wherein said composition is administered to the animal other than the human as a medicine bath agent or a feed additive.

* * * * *